United States Patent [19]

Zlotnik

[11] Patent Number: 5,066,328
[45] Date of Patent: Nov. 19, 1991

[54] ANTIMICROBIAL COATING

[75] Inventor: Clifford Zlotnik, West Mifflin, Pa.

[73] Assignee: Unsmoke Systems, Inc., Braddock, Pa.

[21] Appl. No.: 491,260

[22] Filed: Mar. 9, 1990

[51] Int. Cl.$^5$ .................. A01N 33/00; A01N 59/20
[52] U.S. Cl. ................... 106/18.32; 106/15.05; 514/187
[58] Field of Search ............ 106/15.05, 16, 18, 18.32; 514/187

[56] References Cited

U.S. PATENT DOCUMENTS

| | | | |
|---|---|---|---|
| 2,561,379 | 7/1951 | Kalberg | 106/16 |
| 2,608,556 | 8/1952 | Kalberg | 106/18.31 |
| 2,769,006 | 10/1956 | Kalberg | 106/16 |
| 3,686,331 | 8/1972 | O'Brien et al. | 106/18.31 |
| 3,918,981 | 11/1975 | Long | 106/18.31 |
| 4,656,060 | 4/1987 | Krzyzewski | 106/15.05 |
| 4,766,113 | 8/1988 | West et al. | 514/187 |

*Primary Examiner*—William R. Dixon, Jr.
*Assistant Examiner*—Anthony J. Green
*Attorney, Agent, or Firm*—Reed Smith Shaw & McClay

[57] ABSTRACT

The present invention is directed to an antimicrobial mixture of copper-8-quinolinolate mixed with a binder composition that imparts sufficient fluidity to the copper-8-quinolinolate to permit the mixture to be applied as liquid and to adhere to air passageways, preferably metal, fiberglass or plastic media, such as building heat, ventilation and air conditioning ductwork.

4 Claims, No Drawings

ANTIMICROBIAL COATING

FIELD OF THE INVENTION

The present invention relates to a novel antimicrobial coating in general, and specifically to an antimicrobial mixture comprising copper-8-quinolinolate mixed with a binder composition.

BACKGROUND OF THE INVENTION

Building technology in the last 20 years or so has facilitated the design of architecturally appealing and dramatic, yet functional, office buildings. A major advance over the past 20 years has been the guarantee of a controlled climate in new buildings through the use of self-contained heating, ventilation and air conditioning systems, generally referred to as HVAC systems.

Such advances in office building climate control, however, have not occurred without resultant problems. While the control of the quality of air within buildings limits contact of its occupants with external pollutants, it does place the occupants within the building at risk for potential airborne infectious agents that may be efficiently spread by the HVAC system.

Recently, there has been an outbreak in certain buildings around the United States of common diseases and infections contracted by occupants of these buildings, with the problems being called the "sick building syndrome." The sick building syndrome is typically taken to describe an office building in which complaints of ill health by its occupants are more common than might reasonably be expected to occur in such building occupant population. The affected buildings are commonly those office buildings that have full building air conditioning.

Symptoms exhibited by the occupants in such sick buildings frequently include nasal, eye and mucous membrane symptoms with lethargy, dry skin, headaches and nausea. Several causes have been postulated for such symptoms, and despite much research, no satisfactory explanation of the sick building syndrome has been identified. The postulated causes include formaldehyde from ceiling and wall insulation, furniture and carpet adhesives, cigarette smoke, excess of airborne particles, excess carbon dioxide, bacterial in the air from contamination of the humidifiers in the HVAC system and poor circulation of air through the HVAC system of the building.

There exists a need to treat the HVAC systems of office buildings with an antimicrobial composition to address the sick building syndrome and especially the duct work of such systems. However, to date no suitable antimicrobial composition have been developed that will adhere to the interior of the metal, fiberglass and plastic ducts of HVAC systems.

Although copper-8-quinolinolate is known for use as a fungicide in paints, sealers, lacquers and varnishes, it is not known as an antimicrobial agent in general, or for use in an antimicrobial mixture used to coat ductwork. An antimicrobial mixture has now been developed that contains copper-8-quinolinolate and that can be applied to air passageways in general, and more specifically to metal, fiberglass or plastic ductwork and other metal and plastic media. Buildings in which the air passageways and other ductwork are treated with the antimicrobial mixture of the invention exhibit a lessening in the sick building syndrome.

SUMMARY OF THE INVENTION

The present invention relates to an antimicrobial mixture comprising copper-8-quinolinolate mixed with a binder composition, said binder composition imparting sufficient fluidity to the copper-8quinolinolate to permit the mixture to be applied as a liquid and to adhere to metal, fiberglass or plastic media, such as building ductwork and other air passageways. In a most preferred embodiment of the invention, the binder composition comprises dioctyl sulfosuccinate sodium salt, water, ethanol and substituted hydantoin.

DETAILED DESCRIPTION OF THE INVENTION

The antimicrobial mixture of the present invention comprises copper-8-quinolinolate, mixed with a binder composition, the binder composition imparting sufficient fluidity to the copper-8-quinolinolate/binder composition mixture to permit the mixture to be applied as a liquid and to adhere to metal or plastic media.

Copper-8-quinolinolate is commercially available. The copper-8-quinolinolate is preferably present in the mixture in from about 0.25 to 10% weight of the mixture, and most preferably is present in from about 1 to 4% weight of the mixture.

The binder composition suitable in the antimicrobial mixture of the invention may be any binder composition that imparts sufficient fluidity to the copper-8-quinolinolate to permit the mixture to be applied as a liquid and to adhere to metal or plastic media. Preferably, the binder composition comprises a mixture of dioctyl sulfosuccinate sodium salt, water, ethanol, and a substituted hydantoin. In a most preferred embodiment, the binder composition comprises 40 to 60 wt.% dioctyl sulfosuccinate sodium salt, 15 to 40 wt.% water, 4 to 15 wt.% ethanol and 5 to 20 wt.% substituted hydantoin.

Other suitable binder compositions include sodium polyacrylate, carboxyvinyl polymers, acrylamide copolymers, polyacrylamides, dimethythydantoin formaldehyde resins, polyvinyl alcohol, phenolformaldehyde resins, polyvinylpyrrolidone, vinylpyrrolidone/vinylacetate copolymers, styrene/maleic anhydride copolymer salts and other latex polymers and copolymers.

The antimicrobial mixture of the invention can be applied in liquid form to virtually any metal, fiberglass or plastic media by spraying, misting or painting the mixture on the media. The mixture is useful in coating air passageways, such as void areas above suspended ceilings or surfaces, and is especially useful in coating metal, plastic and fiberglass ductwork in buildings. The antimicrobial mixture may be applied to the air passageways and ductwork by conventional spray painting or misting techniques. Buildings in which the ductwork has been coated internally with the antimicrobial composition of the invention exhibit a significant lessening of the sick building syndrome, and their occupants report fewer ailments and complaints about their health and general well being.

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. An amtimicrobial mixture comprising:

(a) copper-8-quinolinolate present in from about 0.25 to 10% by weight, mixed with (b) a binder composition comprising about 50 to 60 wt.% dioctyl sulfosuccinate sodium salt, about 15 to 40 wt.% water, about 4 to 15 wt.% ethanol, and about 5 to 20 wt.% substituted hydantoin, said binder composition imparting sufficient fluidity to the copper-8-quinolinolate to permit the mixture to be applied as a liquid and to adhere to metal, fiberglass or plastic media.

2. The antimicrobial mixture of claim 1 wherein the copper-8-quinolinolate is present in from about 1 to 4% by weight.

3. An air passageway coated with an antimicrobial mixture comprising:

(a) copper-8-quinolinolate present in from about 0.25 to 10% by weight, mixed with (b) a binder composition comprising about 40 to 60 wt.% dioctyl sulfosuccinate sodium salt, about 15 to 40 wt.% water, about 4 to 15 wt.% ethanol, and about 5 to 20 wt.% substituted hydantoin, said binder composition imparting sufficient fluidity to the copper-8-quinolinolate to permit the mixture to be applied as a liquid and to adhere to the air passageway.

4. The air passageway of claim 3 wherein the copper-8-quinolinolate of the antimicrobial mixture is present in from about 1 to 4% by weight.

* * * * *